US009127026B2

(12) United States Patent
Mariot et al.

(10) Patent No.: US 9,127,026 B2
(45) Date of Patent: Sep. 8, 2015

(54) METHOD FOR PREPARING A SILICA GRAFTED WITH AN ORGANOSILICON COMPOUND

(75) Inventors: David Mariot, Lyons (KR); François Ganachaud, Decines (FR)

(73) Assignees: BLUESTAR SILICONES FRANCE SAS, Lyons (FR); UNIVERSITE MONTPELLIER 2, SCIENCES ET TECHNIQUES, Montpellier (FR); ECOLE NATIONALE SUPÉRIEURE DE CHIMIE DE MMONTPELLIER, Montpellier (FR); CENTRE NATIONAL DE LA RECHERCHE SCIENTIFIQUE (C.N.R.S.), Paris (FR)

( * ) Notice: Subject to any disclaimer, the term of this patent is extended or adjusted under 35 U.S.C. 154(b) by 0 days.

(21) Appl. No.: 14/238,631

(22) PCT Filed: Aug. 16, 2012

(86) PCT No.: PCT/EP2012/066021
§ 371 (c)(1),
(2), (4) Date: May 1, 2014

(87) PCT Pub. No.: WO2013/024137
PCT Pub. Date: Feb. 21, 2013

(65) Prior Publication Data
US 2014/0303331 A1    Oct. 9, 2014

(30) Foreign Application Priority Data
Aug. 16, 2011 (FR) .................................. 11 57357

(51) Int. Cl.
C08G 77/38 (2006.01)
C07F 7/21 (2006.01)
C09C 1/30 (2006.01)

(52) U.S. Cl.
CPC . *C07F 7/21* (2013.01); *C08G 77/38* (2013.01); *C09C 1/3081* (2013.01); *C01P 2002/86* (2013.01); *C01P 2002/88* (2013.01); *C01P 2002/89* (2013.01)

(58) Field of Classification Search
None
See application file for complete search history.

(56) References Cited

U.S. PATENT DOCUMENTS

| 2,938,009 | A | * | 5/1960 | Lucas | 523/212 |
| 3,004,859 | A | * | 10/1961 | Lichtenwalner | 106/490 |
| 3,799,962 | A | * | 3/1974 | Lewis | 556/457 |
| 3,847,848 | A | * | 11/1974 | Beers | 523/213 |
| 4,256,730 | A | * | 3/1981 | Benedict | 424/52 |
| 4,849,022 | A | * | 7/1989 | Kobayashi et al. | 106/490 |
| 4,950,502 | A | * | 8/1990 | Saam et al. | 427/213.36 |
| 5,013,585 | A | * | 5/1991 | Shimizu et al. | 427/220 |
| 5,094,829 | A | * | 3/1992 | Krivak et al. | 423/339 |
| 5,686,054 | A | * | 11/1997 | Barthel et al. | 423/335 |
| 5,830,841 | A | * | 11/1998 | Surutzidis et al. | 510/438 |
| 5,908,660 | A | * | 6/1999 | Griffith et al. | 427/220 |
| 5,919,298 | A | | 7/1999 | Griffith et al. | |
| 6,090,439 | A | * | 7/2000 | Menon et al. | 427/215 |
| 6,344,240 | B1 | * | 2/2002 | Menon et al. | 427/220 |
| 6,800,413 | B2 | * | 10/2004 | Barthel et al. | 430/108.3 |
| 7,109,256 | B2 | * | 9/2006 | Amano et al. | 523/212 |
| 7,713,626 | B2 | * | 5/2010 | Meyer et al. | 428/404 |
| 8,293,834 | B2 | | 10/2012 | Meyer et al. | |
| 2002/0095011 | A1 | * | 7/2002 | Kobayashi et al. | 525/100 |
| 2007/0276078 | A1 | * | 11/2007 | Pottier et al. | 524/492 |
| 2008/0021152 | A1 | * | 1/2008 | Rautschek et al. | 524/588 |
| 2008/0070140 | A1 | * | 3/2008 | Fomitchev et al. | 430/108.3 |
| 2010/0105818 | A1 | * | 4/2010 | Meyer et al. | 524/267 |
| 2010/0152349 | A1 | * | 6/2010 | Meyer et al. | 524/261 |
| 2010/0168276 | A1 | | 7/2010 | Pottier et al. | |
| 2011/0244382 | A1 | * | 10/2011 | Christopher et al. | 430/105 |

FOREIGN PATENT DOCUMENTS

| EP | 0 125 418 | 11/1984 |
| GB | 2001303 | 1/1979 |

OTHER PUBLICATIONS

Berrod et al. "Reinforcement of Siloxane Elastomers by Silica. Chemical Interactions between an Oligomer of Poly(dimethylsiloxane) and a Fumed Silica", J. Appl. Polym. Sci. 26, 833-845, 1981.*
Fu et al. "Surface Reaction of Particulate Silica with Polydimethylsiloxanes" J. Polym. Sci: Polym. Chem. Ed. 19, 3069-3079, 1981.*
International Search Report for PCT/EP2012/066021 dated Oct. 11, 2012.
French Search Report for FR 754848 dated Apr. 4, 2012.

* cited by examiner

*Primary Examiner* — Robert S Loewe
(74) *Attorney, Agent, or Firm* — B. Aaron Schulman, Esq.; Stites & Harbison, PLLC.

(57) ABSTRACT

The present invention relates to a method for preparing a silica grafted with an organosilicon compound, to a grafted silica obtained according to said method and to the use thereof in compositions of silicone crosslinkable into an elastomer.

22 Claims, No Drawings

METHOD FOR PREPARING A SILICA GRAFTED WITH AN ORGANOSILICON COMPOUND

The invention relates to a method for preparing silica grafted with an organosilicon compound. The invention relates more particularly to a method for preparing silica grafted with an organosilicon compound which is simple to use, energy-efficient and suitable for grafting non-functionalised or functionalised, organosilicon compounds, notably vinyl.

The invention also relates to a silica grafted with an optionally functionalised organosilicon compound, along with the use thereof in compositions, notably in silicone elastomer compositions.

Silicone elastomers are synthetic elastomers offering a good compromise between mechanical and chemical properties.

However, the mechanical properties of silicone elastomers alone, notably the tear strength and tensile strength, are insufficient in relation to the industrial applications wherein they are used.

A solution for reinforcing these properties consists of incorporating a filler in the silicone elastomer, known as a reinforcing filler. This filler is notably silica, in a fumed form or in a precipitated form.

However, the reinforcing fillers used are prepared using methods requiring high temperatures, which are thus energy-intensive. Furthermore, the presence of this filler may induce excessive hardening of the silicone elastomer, thus giving rise to problems in respect of the storage and subsequent use thereof.

Various silica surface treatments have thus been envisaged, in order to render the silica hydrophobic and enhance the compatibility thereof with silicone elastomers.

The document DE 10 2007 024094 describes a silica treated with a cyclic polysiloxane, along with a method for preparing such a silica by means of a reaction between the silica and the cyclic polysiloxane. This document mainly discloses a step for spraying cyclic polysiloxane on the surface of the silica.

The document FR 2 395 952 describes a method for preparing, by means of a wet process at a basic pH, a silica grafted with an organosilane compound, comprising mixing of the silica with the organosilane compound, followed by an annealing step. The presence of these this annealing step is penalising for the use of the method and costly in terms of energy.

The document EP 1 559 744 also describes a method for preparing, by means of a wet process at a basic pH, a silica grafted with an organosilane compound, comprising mixing of the silica with the organosilane compound. The document mainly discloses a further annealing step.

The documents EP 0 928 818 and EP 0 900 829 describe a method for preparing, by means of a wet process at an acidic pH, a silica grafted with an organosilane compound, comprising mixing of the silica with the organosilane compound, but without any necessary annealing step. However, this method requires numerous washes of the silica to increase the pH thereof, and the fact that the method is performed at an acidic pH requires expensive equipment to resist corrosion.

In this way, a first aim of the invention is that of providing a method for preparing silica so as to render same hydrophobic, by grafting organosilicon compounds, which does away with the known drawbacks of the prior art mentioned above.

A further aim of the invention is that of providing a method for preparing silica grafted with an organosilicon compound which is simple to use and energy-efficient.

A further aim of the invention is that of providing a method for preparing silica grafted with an organosilicon compound, suitable for grafting non-functionalised or functionalised organosilicon compounds, of variable chain lengths.

A further aim of the invention is that of providing a method for preparing silica grafted with an organosilicon compound, the grafting being homogeneous on the surface of said silica.

A further aim of the invention is that of providing a method for preparing silica grafted with an organosilicon compound, said silica being suitable for ready incorporation in silicone elastomer compounds.

In this way, the invention first relates to a method for preparing a silica grafted with at least one organosilicon compound chosen from the group consisting of:
  a cyclosiloxane,
  a bi-silanol compound having the formula $R_2Si(OH)_2$, the groups R, identical or different, representing a $C_1$-$C_{10}$ alkyl group, preferably $C_1$-$C_3$, advantageously a methyl, an alkenyl group, preferably vinyl, an aryl group, preferably phenyl,
  a polyorganosiloxane having the following formula (I):

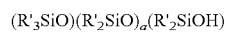

wherein:
  the groups R', identical or different, represent a $C_1$-$C_{10}$ alkyl group, preferably $C_1$-$C_3$, advantageously a methyl, an alkenyl group, preferably vinyl, an aryl group, preferably phenyl or an —OH group,
  and the symbol a is an integer between 1 and 30 and preferably between 3 and 30,
  and mixtures thereof;
  said method comprising the following steps:
  a) the preparation of an aqueous mixture having a pH between 6 and 11, preferably between 6.5 and 9.5 and more preferentially of approximately 7, by adding in an aqueous medium (preferably water) a silica and optionally a base,
  b) the said organosilicon compound is added to the mixture,
  c) the mixture is refluxed for a time greater than or equal to 1 hour, preferably greater than or equal to 20 hours, and at a temperature between 50° C. and 100° C., preferably between 70° C. and 100° C., and
  d) the grafted silica is separated from the mixture.

According to one preferred embodiment, the step a) is broken down into two steps as follows:
  $a^1$) a mixture is prepared by adding a silica to an aqueous medium, and
  $a^2$) a base is added to the mixture such that the pH of the mixture is between 6 and 11, preferably between 6.5 and 9.5 and more preferentially such that the pH of the mixture is equal to approximately 7.

According to one preferred embodiment, the method according to the invention comprises a further step a') performed between steps a) and b) consisting of adding to the mixture:
  a water-miscible solvent compatible with said organosilicon compound so as to facilitate contact between the organosilicon compound and the silica, preferably chosen from the group consisting of: ethanol, isopropanol, tetrahydrofuran, methyl ethyl ketone, and mixtures thereof, and/or a salt, preferably chosen from the group consisting of sodium, potassium, ammonium, pyridinium salts and mixtures thereof.

This solvent may be chosen from the group consisting of ethanol, isopropanol, tetrahydrofuran, methyl ethyl ketone, and mixtures thereof. In one preferred embodiment, the water-miscible solvent is isopropanol.

According to the invention, the water-miscible solvent may be used in a quantity by weight ranging from 10 to 50%, preferably from 20 to 40%, in relation to the weight of aqueous medium, silica and organosilane compound.

According to the invention, the percentage by weight of the salt/silica ratio is between 0.1 and 10%, preferably between 0.5 and 5%.

According to a further preferred embodiment, the method according to the invention comprises a further step c') performed between steps c) and d) consisting of adding a non-water miscible solvent to the mixture. The addition thereof is notably suitable for transferring the hydrophobic silica produced therein, before filtration.

This non-water-miscible solvent may be chosen from low molecular weight silicones such as hexamethyldisiloxane, octamethylcyclotetrasiloxane, diphenyltetramethyldisiloxane or silicone oils with trimethyl terminal groups. Furthermore, further water-immiscible solvents may be used, such as aromatic solvents such as toluene and xylene, heptane or any other linear, branched or cyclic saturated hydrocarbons, ethers, such as diethylether, halogenoalkanes such as chloroform or ketones such as methyl isobutyl ketone.

Alternatively, the method according to the invention comprises the sequence of steps a), preferably $a^1$) and $a^2$), followed by a'), b), c), c'), and d).

In one preferred embodiment of the invention, the following steps are performed after step d):

e) the grafted silica from step d) is dried, and f) the grafted silica is ground.

Preferably, the method comprises the sequence of steps a), preferably $a^1$) and $a^2$), followed by a'), b), c), c'), and f).

According to the invention, the silica may be a fumed silica or a precipitated silica. Advantageously, the silica is a fumed silica. When such a silica is used, the use of a base to adjust the pH in step a) is preferable. Preferably, this step a) is broken down into steps $a^1$) and $a^2$) mentioned above.

Advantageously, the silica has a BET specific surface area at 25° C. between 40 and 400 m²/g. The specific surface area may be measured using the Brunauer-Emmet-Teller method described in Journal of American Chemical Society vol 60, p.309, February 1938.

As an example of fumed silica, the product sold under the reference Aerosil© A200 by Evonik may be chosen.

According to the invention, the organosilicon may be chosen from optionally functionalised cyclosiloxanes, and mixtures thereof.

In one embodiment of the invention, the cyclosiloxane is advantageously chosen from cyclosiloxanes comprising 3 to 7 silicon atoms, preferably a cyclotetrasiloxane.

According to one advantageous embodiment of the invention, the cyclosiloxane has the following formula (II):

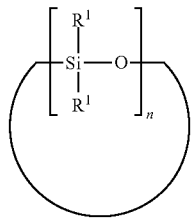

(II)

where:

n=3, 4, 5, 6, 7 or 8; and:

if the cyclosiloxane is a non-functionalised cyclosiloxane, the symbols $R^1$, identical or different, represent an optionally substituted linear or branched $C_1$-$C_{12}$ alkyl radical, an optionally substituted $C_5$-$C_{10}$ cycloalkyl radical, an optionally substituted $C_6$-$C_{18}$ cycloalkyl radical or an optionally substituted aralkyl radical, and if the cyclosiloxane is a functionalised cyclosiloxane, at least one of the symbols $R^1$ represents an alkenyl radical, preferably $C_2$-$C_4$ and more preferentially a vinyl radical.

In one preferred embodiment, the cyclosiloxane is octamethylcyclotetrasiloxane or tetramethyltetravinylcyclotetrasiloxane, or a mixture of the two.

In one preferred embodiment, a mixture of organosilicon compounds is used, comprising:

at least one non-functionalised cyclosiloxane having formula (II) as defined above, and at least one functionalised cyclosiloxane having formula (II) as defined above.

According to the invention, the content by weight of the functionalised cyclosiloxane, notably vinyl, in the non-functionalised and functionalised cyclosiloxane may vary in larges proportions. Advantageously, this content may vary between 0.01 and 50%, notably between 0.1 and 20%, preferably between 0.1 and 12%, more preferably between 0.2 and 6%, preferentially between 0.25 and 3%.

In one embodiment, the organosilicon compound is chosen from bi-silanol compounds having the formula $R_2Si(OH)_2$, the groups R, identical or different, representing a $C_1$-$C_{10}$ alkyl group.

In one embodiment, the groups R represent a $C_1$-$C_3$ alkyl group, advantageously a methyl.

In one embodiment, the groups R represent an alkenyl group, preferably vinyl, or an aryl group, preferably phenyl.

In a further embodiment, the bi-silanol comprises:

a group R representing a $C_1$-$C_3$ alkyl group, advantageously a methyl, and a group R representing an alkenyl group, preferably vinyl, or an aryl group, preferably phenyl.

For example, the invention uses a bi-silanol wherein the two groups R are methyls or vinyls, or a bi-silanol comprising a vinyl and a methyl.

In one embodiment, the organosilicon compound is chosen from the compounds having the formula $(R'_3SiO)(R'_2SiO)_a(R'_2SiOH)$, the groups R', identical or different, representing a $C_1$-$C_{10}$ alkyl group, where a is between 1 and 30, preferably between 3 and 30.

In one embodiment, the groups R' advantageously represent a $C_1$-$C_3$ alkyl group, preferably a methyl.

In one embodiment, the groups R' represent an alkenyl group, preferably vinyl, an aryl group, preferably phenyl or an —OH group.

In a further embodiment, the compound having the formula $(R'_3SiO)(R'_2SiO)_a(R'_2SiOH)$ comprises:

at least one group R' representing a $C_1$-$C_3$ alkyl group, preferably a methyl, and at least one group R' representing an alkenyl group, preferably vinyl, an aryl group, preferably phenyl or an —OH group.

In one advantageous embodiment, this compound comprises:

at least one vinyl group, the remainder of the groups R' being methyl groups.

In one embodiment, a salt is added to the mixture from step a), preferably to the mixture from step $a^1$). This salt is advantageously chosen from the group consisting of sodium, potassium, ammonium, Bis(triphrnylphosphoranylidene)ammonium, phosphonium salts, cryptants (e.g. Kryptofix®222, CAS No. 23978-09-8) and mixtures thereof. According to the invention, the salt is a chloride, and is advantageously NaCl.

In one embodiment, the molar concentration of salt in the mixture is between 0.01 and 10 mol/L, preferably between 0.1 and 1 mol/L.

The invention further relates to a silica grafted with at least one organosilicon compound obtained or suitable for being obtained by means of the method according to the invention. The invention further relates to a silica grafted with at least one organosilicon compound, characterised by the presence on the surface of Si—O-G functions where G is a siloxane graft comprising:

i) at least two siloxyl D units having the formula $(R^1)_2 SiO_{2/2}$, ii) and one terminal siloxyl $D^{OH}$ unit having the formula $(R^1)_2(OH)SiO_{1/2}$, wherein the symbols $R^1$, identical or different, represent an optionally substituted linear or branched $C_1$-$C_{12}$ alkyl radical, an optionally substituted $C_5$-$C_{10}$ cycloalkyl radical, an optionally substituted $C_6$-$C_{18}$ aryl radical or an optionally substituted aralkyl radical or an alkenyl radical, preferably $C_2$-$C_4$.

In one embodiment, the siloxane graft G comprises between 2 and 31 D siloxyl units and at least one terminal siloxyl $D^{OH}$ unit.

The invention notably relates to a silica grafted with at least one organosilicon compound, characterised by the presence on the surface of Si—O-G functions where G is a siloxane graft comprising:

i) 3 siloxyl D units having the formula $(CH_3)_2SiO_{2/2}$ and 1 $D^{OH}$ terminal siloxyl unit having the formula $(CH_3)_2(OH)SiO_{1/2}$, or ii) 3 siloxyl $D^{Vi}$ units having the formula $(CH_3)(CH_2\!\!=\!\!CH_2\text{-})SiO_{2/2}$ and 1 terminal siloxyl $D^{OH}$ unit having the formula $(CH_3)_2(OH)SiO_{1/2}$.

In one embodiment, the silica carries on the surface Si—O-G functions from the two categories i) and ii).

The invention also relates to a grafted silica suitable for being obtained by means of the method according to the invention, notably any of the silicas described above, characterised by:

i) thermogravimetic analysis (TGA) with a temperature rise of 50° C. per minute and measured between 200° C. and 450° C., of a mass loss greater than or equal to 0.55%, preferably between 0.55 and 3%, ii) thermogravimetic analysis (TGA) with a temperature rise of 50° C. per minute and measured at a temperature greater than 450° C., of a mass loss obtained greater than 1.1%, and iii) the presence of a peak between −5 and −15 ppm in a spectrum obtained by means of nuclear magnetic resonance of the chemical element $^{29}$Si in the solid state.

The NMR spectra of the solid $^{29}$Si were obtained on a wide-bore type 400 MHz spectrometer. The frequency of $^{29}$Si is in this instance 79.49 MHz. The samples were packaged in $ZrO_2$ rotor 7.5 mm in outer diameter. The rotational speed at the magic angle is 5000 Hz. The sequence mainly used is a one-pulse sequence with proton decoupling (annotated OP).

Direct observation of the silicon (one-pulse, referred to as OP-MAS mode) enables an overall measurement of the silicon species present on the surface of the silica (chemically grafted and/or physisorbed). The acquisition settings used were: pulse Pi/6 for a duration of 1 μs, relaxation interval D1=60 s. The total experiment time varies from 6 hours to 24 hours.

The thermogravimetric analyses (TGA) are performed with a temperature gradient of 50° C. per minute in nitrogen.

The aim of the grafted silica according to the invention is that of being further used in the preparation of crosslinked liquid or pasty silicone compositions, preferably by polyaddition or polycondensation, into silicone elastomer in the ambient atmosphere at normal temperatures or at higher temperatures, or non-reactive (anti-foaming) liquid or pasty silicone compositions.

The invention thus also relates to a silicone composition crosslinkable into an elastomer comprising at least one grafted silica according to the invention.

Advantageously, the content by weight of grafted silica in relation to the total weight of the composition is between 0.1 and 80% by weight, preferably between 1 and 50% by weight.

In one embodiment, the grafted silica according to the invention is used in a method for obtaining a silicone composition suitable for crosslinking by polyaddition, characterised in that it consists of mixing the following products:

a grafted silica according to the invention one or a plurality of polyorganosiloxanes (POS) (I)

one or a plurality of POS (II), optionally one or a plurality of POS (III), suitable for use as diluent(s)

a catalytic system comprising a catalyst, preferably platinum-based, and optionally an inhibitor or retardant.

The POS (I) may notably be chosen from the polydiorganosiloxane oils carrying Si-alkenyl particularly Si-vinyl in and/or at the ends of the chain. Mention may be made for example of α,ω-divinyl polydialkyl (methyl) siloxane.

Advantageously, the POS (I) is a vinyl POS (I) carrying at least two Si-vinyl units per molecule, preferably at least three per molecule, when the POS (II) merely comprises two SiH units per molecule.

The POS (II) may notably be chosen from the polyorganohydrogenosiloxanes comprising at least two ≡SiH units per molecule, preferably at least three when the POS (I) merely comprises two ≡Si-vinyl units per molecule. Mention may be made for example of polyalkyl(methyl)hydrogenosiloxane or branched hydrogenated POS comprising tri or tetrafunctional units and ≡SiH units.

The POS (III) may be polydiorganosiloxane, such as a polyalkyl preferably trimethylsilyl-terminated polydimethylsiloxane.

The platinum-based catalyst may notably consist of a platinum complex such as that prepared using chloroplatinic acid and divinyl-1,3-tetramethyl-1-1-3-3-disiloxane, according to the U.S. Pat. No. 3,814,730 (Karstedt's catalyst). Further platinum complexes are described in the U.S. Pat. Nos. 3,159,601, 3,159,662 and 3,220,972.

The inhibitors may be chosen from polyorganosiloxanes, advantageously cyclic, substituted with at least one alkenyl, tetramethylvinyltetrasiloxane being particularly preferred, pyridine,
phosphines and organic phosphites,
unsaturated amides,
alkylated maleates,
and acetylenic alcohols, such as those described in the documents FR 1528464 and FR 2372 74.

According to a first alternative embodiment of the method as defined above:
the composition is produced, in the form of a bicomponent system $C_1$ and $C_2$ intended to be placed in contact with each other to produce a crosslinked elastomer by polyaddition between the POS (I) and (II),
and measures are taken to ensure that only one of the parts $C_1$ or $C_2$ contains catalyst and optionally either of the POS (I) and (II).

According to a second alternative embodiment of this method for preparing crosslinkable liquid compositions, a single-component system intended to be crosslinked in ambient air and/or under the effect of temperature is produced.

Advantageously, the crosslinking is performed at a temperature greater than or equal to 150° C., preferably between 150° C. and 200° C.

These crosslinkable elastomer precursor compositions may also comprise one or a plurality of functional additives, such as for example a non-reinforcing filler consisting of chalk, quartz powder, diatomaceous earth, mica, kaolin, aluminas or iron oxides.

The additives may also be chosen from pigments, anti-adhesive agents, des plasticisers or rheology modifiers, stabilisers or adherence promoters.

The mixtures involved in these methods may be produced using suitable known devices, notably conventional mixers used routinely for these preparations, such as:
arm mixers,
internal mixers,
planetary mixers,
ploughshare mixers,
co or counter-rotating dual shaft mixers,
continuous extrusion mixers,
or duplex mixers.

The mixtures involved in these methods may also be produced using further batch or continuous devices, such as stirred reactors or static mixers.

The present application further relates to a silicone elastomer obtained by crosslinking a crosslinkable silicone composition into elastomer according to the invention.

The present application further relates to an article based on a silicone elastomer according to the invention.

According to the invention, the article may be applied in various fields, such as contacts for electronic computers and telephone keys, computer keyboards, etc.

The present application further relates to a toothpaste composition comprising a grafted silica according to the invention.

The present application further relates to an anti-foaming composition comprising a grafted silica according to the invention. The grafted silica content in the anti-foaming composition may be between 1 and 10% by mass, preferably between 3 and 7% by mass.

The present invention will be understood more clearly on reading the following examples. These examples are given as an indication and are in no way limiting.

EXAMPLE 1

Production of Silica Grafted with a Non-Functionalised Cyclotetrasiloxane According to the Invention The method described hereinafter was performed in a 3 L reactor with dual-shaft stirring and a baffle.

800 g of deionised water was first introduced into a 3 L reactor. Under stirring at 400 rpm, 120 g of Aerosil© A200 fumed silica was then dispersed in water.

A further 400.9 g of deionised water was then added followed by 0.9197 g of NaCl salt. The stirring was reduced to 200 rpm and then left overnight.

6 ml of a soda solution containing approximately 1 mol/l was added to reach a pH close to neutrality. Although the dispersion is not completely fluid since it forms a gel, the pH of this gel was measured at a value of approximately 7.2.

399.2 g of isopropanol (IPA), followed by 270.4 g of octamethylcyclotetrasiloxane ($D_4$) were then added. Under stirring at 600 rpm, the medium was refluxed at 80° C. for 24 hours. A kinetic study was performed and indicated that the grafting indeed takes place covalently and progressively, since it is observed that integration of the silanol peaks declines in favour of an increase in the peak intensity of the grafting D units (having the formula $(R^1)_2SiO_{2/2}$).

The entire reactor was then drained into a can. The reactor was then washed with 2 L of water, 200 ml of IPA and 500 ml of heptane. The silica was then retrieved by filtration with a pressure of 2 bar and filter board (pore diameter: 20 μm). The silica was then air-dried under the hood, then 4 hours 50° C. in a vacuum, and then overnight at 60° C. in a vacuum followed by 5 hours at 90° C. in a vacuum. The dried silica was then placed in a can, and the silica clusters broken up by mechanical action.

EXAMPLE 2

Production of Silica Grafted with a Non-Functionalised Cyclotetrasiloxane According to the Invention (Ex-2)

A similar method to that described in example 1 was performed with 170 g of Aerosil© A200 fumed silica, 1700 g of deionised water, 1.3029 g of NaCl and 202 g of IPA. Soda was then added to reach a pH of 7.3.

362.2 g of IPA was then added followed by 383.01 g of $D_4$. After 24 hours at 80° C., the silica was filtered at a pressure of 2 bar and a filter board (pore diameter: 20 μm). The silica remaining in the reactor was retrieved using a biphasic water/heptane mixture. Only the heptane phase was retrieved and filtered to retrieve all the silica.

The filtered silica was then placed in an oven to dry in a vacuum for 48 hours at 90° C. The dried silica was then placed in a can, and the silica clusters broken up by mechanical action.

EXAMPLE 3

Production of Silica Grafted with a Non-Functionalised Cyclotetrasiloxane According to the Invention (Ex-3)

The same protocol as that followed for example 1 was used. The only difference was in the heating time which was halved, i.e. 12 hours of reflux at 80° C. instead of 24 hours.

EXAMPLE 4

Production of Silica Grafted with a Non-Functionalised Cyclotetrasiloxane According to the Invention (Ex-4)

The method was implemented in the absence of salt and isopropanol, in a 3 L reactor with dual-shaft stirring and a baffle.

In this way, 170.4 g of Aerosil© A200 fumed silica was dispersed in 1700 g of deionised water. 4.6 ml of a concentrated soda solution was added so that the silica dispersion reached a pH of 6.99. 1218.7 g of $D_4$ was then added and the mixture was heated to 80° C. for 24 hours.

After 24 hours at 80° C., a portion of the silica was retrieved by vacuum filtration using a No. 4 sintered filter; the other portion with a rotary evaporator with a 5 mbar vacuum, and a progressive temperature rise (from 60° C. to 120° C.). The silica retrieved by filtration and that dried with a rotary evaporator were then placed in an oven for 24 hours at 90° C. in a vacuum. The dried silica was then placed in a can, and the silica clusters broken up by mechanical action.

EXAMPLE 5

Production of Silica Grafted with a Non-Functionalised Cyclotetrasiloxane According to the Invention (Ex-5)

The method was used without IPA, but with a crowded cation (tetrabutyl ammonium bromide or TBABr) and a large quantity of $D_4$, acting both as the solvent and reagent.

24 g of silica was first dispersed in 600 g of water in a 1 liter reactor, the pH is then 3.54. 0.6769 g of TBABr (i.e. a concentration of $4.10^{-3}$ mol/l) was then added and the pH brought to 7 by adding 1 mol/l soda (approximately 1 ml) and approximately 1 ml of 0.1 mol/l soda.

Once the pH of the dispersion had neutralised, 200 g of $D_4$ was then added into the reactor. The mixture was then refluxed at 100° C. for 24 hours. The hydrophobic silica was then retrieved by adding approximately 120 ml of heptane. The silica was then washed with 3 centrifugation/redispersion cycles in heptane and placed to air-dry for 15 hours followed by 24 hours in an oven at 90° C. in a vacuum.

COMPARATIVE EXAMPLE 1

Production of Silica Grafted with a Non-Functionalised Cyclotetrasiloxane in Concentrated Acid Medium (C-Ex 1)

180 g of Aerosil© A200 fumed silica was dispersed in 820 g of water, 180.1 g of concentrated HCl and 334 g of IPA. 25.1 g of $D_4$ was then added and the whole heated at 85° C. for 30 min, and then cooled to ambient temperature (20° C.).

Under these experimental conditions, the silica dispersion was stirred very poorly, since the medium was completely solidified while the dispersion temperature was merely 50° C.

347.1 g of hexamethyldisiloxane ($M_2$) was then added to fluidise the medium. To facilitate phase transfer, approximately 300 ml of heptane was also added. The acidic aqueous phase was then removed, and 1.5 L of water was added and left under stirring in the presence of the silica dispersed in $M_2$ for 30 min.

1.5 L of water and 1.5 g of $NaHCO_3$ were added to wash the silica, which was not sufficient to neutralise the silica, since this washing water had, after discharge, a pH between 1 and 2. 1.5 L of water was then added, but at that stage, excessively vigorous stirring gave rise to emulsification of the medium, making it impossible to separate the organic and aqueous phases merely by settling.

All the silica was then retrieved by vacuum filtration using a No. 4 sintered filter. The silica was then oven-dried at 90° C. in a vacuum. The dried silica was then placed in a can, and the silica clusters broken up by mechanical action.

COMPARATIVE EXAMPLE 2

Production of Silica Grafted with a Non-Functionalised Cyclotetrasiloxane in Concentrated Acid Medium (C-Ex 2)

180.7 g of Aerosil© A200 fumed silica was dispersed in 800.1 g of deionised water, 180 g of concentrated HCl and 333 g of IPA. 130.1 g of $D_4$ was then added and the whole was heated at 85° C. for 30 min, and then cooled to ambient temperature. Under these experimental conditions, the silica dispersion was stirred very poorly, since the medium was completely solidified while the dispersion temperature was merely 45° C.

Under gentle stirring (200 rpm), 426 g of $M_2$ was added. After 1 hour of stirring, it was observed that there are 3 phases in the medium (in addition to the large blocks of silica attached to the wall), silica settled at the bottom of the reactor and silica situated in the phase $M_2$. After 13 hours of stirring, the silica that had settled has still not changed to organic phase, a further 200 g of $M_2$ was added enabling a greater phase change. The acidic aqueous phase was then drained (pH≤1 per paper pH indicator).

1.5 L of water and 1.5 g of $NaHCO_3$ were added to wash the silica, which was not sufficient to neutralise the silica, since this washing water had, after discharge, a pH between 1 and 2. In order to retain the silica dispersed in the phase $M_2$, 500 g of further $M_2$ followed by 3 times 1.5 L of water were added to wash the silica. After stirring, the pH of the water from the final wash was 2.1 (measurement with pH-meter).

A further wash containing 1.5 L of water and 30 g of $NaHCO_3$ was then applied, rendering the medium basic (and not neutral). 4 further washes each with 1 L of water were performed to approach neutrality.

Since silica is difficult to filter, the $M_2$ was evaporated in air (for 48 hours) and the silica was dried in a ventilated oven at 130° C. for 24 hours.

Table I below shows the results of the characterisation of each of the silicas obtained in examples 2 to 5 and comparative examples 1 and 2, along with two industrial silicas: an unprocessed Aerosil© A200 silica (C-Ex 3) and a silica treated by vaporising $D_4$ at high temperatures (C-Ex 4).

TABLE I

| | Mass loss (TGA) (% mass) | | | Ethoxylation | Remaining surface Silanol density (per mm$^2$) | Solid NMR (OP-MAS) | |
|---|---|---|---|---|---|---|---|
| | | | | | | % D$^{OH}$** in graft | % "mobile" D in graft |
| Silica | <200° C. | between 200 and 450° C. | >450° C. | % D* on surface | peaks between −85 and −105 ppm | peak between −5 and −13 ppm | refined peak at around −22 ppm |
| Ex-2 | 0.4 | 0.9 | 1.9 | 7.5 | 2.50 | 10-20% | 0 |
| Ex-3 | 0.7 | 0.6 | 1.4 | 5.2 | 2.60 | 10-20% | 0 |
| Ex-4 | 0.3 | 0.6 | 1.2 | 6.4 | 2.75 | 10-20% | 0 |
| Ex-5 | 1.6 | 2.5 | 20.0 | 25 | 2.20 | 10-20% | 5 |
| C-Ex 1 | 0.4 | 1.2 | 2.9 | 9.2 | 3.60 | 0-5% | 15 |
| C-Ex 2 | 1.0 | 8.1 | 6.3 | 18.1 | 3.00 | 0-5% | 45 |
| C-Ex 3 | 1.0 | 0.5 | 0.7 | 0.2 | 4.00 | 0 | 0 |
| C-Ex 4 | 1.0 | 0.2 | 1.0 | 6 | 2.65 | 0 | 0 |

C-Ex 3: Aerosil © A200 silica: unprocessed, non-grafted silica marketed by Evonik;
C-Ex 4: silica grafted by high-temperature octamethylcyclotetrasiloxane vaporisation;
*% D: mass percentage of D siloxyl units having the formula $(CH_3)_2SiO_{2/2}$;
**$D^{OH}$: siloxyl units having the formula $(CH_3)_2(OH)SiO_{1/2}$;

The thermogravimetric analyses (TGA) were performed on a TA Instrument Q50 unit, in a nitrogen atmosphere (100 ml/min) with a temperature gradient of 50° C. per minute, from ambient temperature (20° C.) to 900° C. Before 200° C., the mass loss consists of water and other physisorbed species (such as for example IPA or $D_4$). Between 200 and 450° C., the mass loss mainly consists of physisorbed and non-chemically grafted linear organosilane compounds. A chemically grafted linear organosilane compound breaks down over 450° C. whereas if it is merely adsorbed, the degradation temperature thereof is lower.

Ethoxylation can be used to quantify the grafting precisely by eliminating the proximity effects of the compounds grafted with the surface observed in TGA. This technique consists of "digesting" the graft in a tetraethylorthosilicate (TEOS) and potassium hydroxide (KOH) solution, i.e. breaking each of the D units chemically grafted or adsorbed on the surface and subsequently quantifying same by means of "headspace" gas chromatography. The results obtained are expressed as a mass grafting percentage.

The NMR spectra of the $^{29}$Si solid were obtained on a wide-bore type 400 MHz spectrometer. The frequency of $^{29}$Si is in this instance 79.49 MHz. The samples were packaged in $ZrO_2$ rotor 7.5 mm in outer diameter. The rotational speed at the magic angle was 5000 Hz. The sequence mainly used is a one-pulse sequence with proton decoupling (annotated OP).

Direct observation of the silicon (one-pulse, referred to as OP-MAS mode) enables an overall measurement of the silicon species present on the surface of the silica (chemically grafted and/or physisorbed).

The signals from the silicon atoms of the silica appear at chemical shifts between −85 and −120 ppm. It is commonly accepted that the signal centred around a chemical shift of −92 ppm is attributed to twin silanols ($Q^2$), the signal centred around a chemical shift of −101.5 ppm is attributed to silanols alone ($Q^3$) (terminal, vicinal and isolated) and the signal centred around a chemical shift of −110 ppm is attributed to surface and core siloxane bridges (Si—O—Si) ($Q^4$). To quantify the silanols present on the surface of the silica after grafting, the following formalism was adopted.

Based on a detailed study published by Zhuravlev (Zhuravlev, L. T., The surface chemistry of amorphous silica. Zhuravlev model. Colloids and Surfaces A: Physicochemical and Engineering Aspects 2000, 173, (1-3), 1-38), a fully hydroxylated silica has a silanol surface density of 4.6 per nm$^2$. An A200 fumed silica hydroxylated for 72 hours in the presence of hydrochloric acid at 60° C. was considered to be fully hydrolysed and thus comprised 4.6 silanols per nm$^2$. The NMR analysis of the silicon with the OP-MAS sequence and deconvolution of the peaks at −92, −101.5 and −110 ppm of the silicon atoms $Q^2$, $Q^3$ and $Q^4$ made it possible to calculate the percentage of the NMR signal corresponding to 4.6 silanols per nm$^2$. The analysis according to the same treated silica method made it possible, by comparing the NMR signal percentages, to quantify the silanols remaining on the silica surface.

The signals from the silicon atoms from grafting the D units appear at chemical shifts between −5 and −25 ppm and the vinyl D units between −20 and −40 ppm. In the range between −5 and −25 ppm, various species may be differentiated:

those for which the peak maximum is situated between −5 and −13 ppm corresponding to the D unit comprising an OH function ($D^{OH}$), those for which the peak maximum is situated between −13 and −20 ppm correspondent to D units close to the silica surface anchor point (as the chemical shift increases in absolute terms, the interaction of the D units with the surface decreases), and the species characterised by a refined peak at around −22 to −22.5 ppm corresponding to D groups ($D^P$) without any interaction with the surface (thus to D units of a silicone chain at a distance from the grafting point or to D units of a physisorbed silicone chain).

The acquisition settings used were: pulse Pi/6 for a duration of 1 μs, relaxation interval D1=60 s. The total experiment time varied from 6 hours to 24 hours.

The silicas Ex-2 and Ex-3 exhibit low mass losses before 200° C., and between 200 and 450° C. This indicates that there are few or no species adsorbed on the silica surface. The mass grafting percentage determined by ethoxylation is situated between 5 and 8% by mass. This result is considerably greater than the mass losses observed by TGA, indicating that the grafting interacts strongly with the surface and that the thermal degradation is incomplete.

The NMR spectra of the silicas Ex-2 and Ex-3 indicate that a majority of surface silanols reacted (there is a significant decrease in the intensity of the NMR signals situated around −90 and −100 ppm). The NMR spectra also exhibit significant signals centred around −10 ppm (the area of this peak represents around 20% of the total area available for grafting), indicating that there is a high concentration of $D^{OH}$ groups.

Furthermore, no refined and intense peak is observed around −22 ppm. The signals of these D groups essentially appear between −13 and −21 ppm; this corroborates that these D units are "close" to the silica surface.

The results of example 4 (Ex 4) demonstrate that grafting took place, despite the absence of salt, thus demonstrating that the presence of a salt is optional for the grafting to be effective. The mass losses and the NMR spectrum profile demonstrate that the grafting is similar to that in examples 2 and 3.

The results of example 5 (Ex-5) demonstrate the influence of adding a cation, notably a crowded cation such as TBABr, on the quantity of grafted organosilane compound (25% by mass of D groups by ethoxylation). Only 5% of this graft appears in the form of a refined peak around −22 ppm. Therefore, there are a small proportion of "mobile" D groups. Given that the surface silanol content is similar to those obtained with silicas Ex 2 to Ex 4 and that the grafting ratio is between 3 and 4 times greater, the chemically grafted linear organosilane compounds have a higher molar mass than on the surface of the silicas Ex 2 to Ex 4. The salt used thus makes it possible to vary the length of the grafted chains.

The presence of a crowded cation (Ex-5) also makes it possible to accelerate the grafting kinetics considerably. In less than 5 hours, the grafting obtained is similar to that for the silica Ex-2 (same silicon NMR profiles and same mass % of D groups).

The silica C-Ex 3 is a non-modified, unprocessed Aerosil© A200 silica. The mass loss before 200° C. consists of physisorbed water. The greater mass losses are attributed to the water created by surface silanol condensation. The NMR spectrum does not show, as expected, any peak in the range of the D units (between −5 and −25 ppm), and a peak intensity corresponding to silanols greater than that of the grafted silicas.

The silica C-Ex 4 is a silica modified with $D_4$ grafted at a high temperature. The OP-MAS $^{29}$Si solid NMR analysis does not exhibit any signal between −5 and −13 ppm, indicating that there are few or no $D^{OH}$ groups. The ethoxylation grafting analyses result in grafting of approximately 7% D units on the surface, whereas by TGA, the mass loss is 1% before 200° C. and 1% above 450° C. The 7% grafting thus includes 1% adsorbed rings, and 6% chemically grafted D units. This major difference between the results obtained with ethoxylation and with TGA thus indicates that the grafting interacts strongly with the silica surface for the silica C-Ex 4.

The grafted silica C-Ex 1 exhibits 1.2% mass loss between 200 and 450° C., which is slightly greater than that obtained with the silica Ex 2 according to the invention, the mass loss being even greater with the silica C-Ex 2. These results demonstrate the significant presence, notably for the silica C-Ex 2, of compounds comprising adsorbed D units not grafted on the silica surface.

The NMR spectra of the silicas C-Ex 1 and C-Ex 2 indicate that a majority of non-reacted silanols remain on the silica surface. Given that the grafting ratio is high (approximately 9 and 18% for the silicas C-Ex 1 and C-Ex 2 respectively) and that there are less surface silanols having reacted in relation to the silicas Ex-2 to Ex-5, the silicone chains comprising D units present on the silica surface are thus longer (greater molar mass), adsorbed, or both. On examining the peak around −22 ppm (characteristic of compounds comprising D units having a high mobility), it is observed that there is a greater proportion of this type of "mobile" D units (between 15 and 45%) on the surface of the silicas C-EX 1 and C-Ex 2 than on the surface of the silicas obtained according to the invention (Ex-2 to Ex-5). The grafting of the silicas C-Ex 1 and C-Ex 2 is also characterised by the small proportion of $D^{OH}$ groups, as observed on the NMR spectra between −5 and −13 ppm. According to this method, the grafted chains are thus either longer (low concentration of $D^{OH}$) or grafted on both sides.

It should also be noted that the silicas Ex-2 to Ex-5 and C-Ex 1, C-Ex 2 and C-Ex 4 are all modified using $D_4$, but according to the methods used, the grafted silicas obtained are different.

EXAMPLE 6.1

Production of Grafted Silica According to the Invention with a Mixture of Cyclotetrasiloxane and Vinyl Cyclotetrasiloxane (Ex 6.1)

In a 250 ml reactor equipped with anvil stirring, 10 g of Aerosil© A200 fumed silica was dispersed in 100 g of water. 0.0765 g of NaCl salt was then added. After 30 minutes of stirring at 500 rpm, the pH of the silica dispersion was neutralised by adding an approximately $10^{-1}$ mol/L soda solution. 33.3 g of IPA was then added followed by 22.06 g of $D_4$ and 0.5305 g of tetra(vinylmethyl)cyclosiloxane ($D_4^{Vi}$) respectively. The medium was then refluxed for 24 hours at 80° C. with stirring at 300 rpm. After cooling, the silica was retrieved by vacuum filtration using a No. 4 sintered filter, and washed twice with heptane. After vacuum-drying at 90° C. for 24 hours, the grafting of the silicas obtained was analysed by solid state silicon NMR, by TGA and by grafting digestion followed by a gas chromatography analysis.

EXAMPLE 6.2

Production of Grafted Silica According to the Invention with a Mixture of Cyclotetrasiloxane and Vinyl Cyclotetrasiloxane (Ex 6.2)

The same method as for example 6.1 was used, except that 21.44 g of $D_4$ and 1.3126 of $D_4^{Vi}$ were added.

EXAMPLE 6.3

Production of Grafted Silica According to the Invention with a Mixture of Cyclotetrasiloxane and Vinyl Cyclotetrasiloxane (Ex 6.3)

The same method as for example 6.1 was used, except that 20.45 g of $D_4$ and 2.6163 of $D_4^{Vi}$ were added

EXAMPLE 7

Production of Grafted Silica with a Vinyl Cyclotetrasiloxane According to the Invention (Ex 7)

The same method as for example 2 was used, except that the 383.01 g of $D_4$ was replaced by 444.6 of $D_4^{Vi}$ and a rotary evaporator drying step at 150° C. in a vacuum of 5 mbar for 4 hours was added.

EXAMPLE 8.1

Production of Grafted Silica with a Mixture of Cyclotetrasiloxane and Vinyl Cyclotetrasiloxane (Ex 8.1)

The same method as for example 2 was used, except that the 383.01 g of $D_4$ was replaced by 382 g of $D_4$ and 1.03 g of $D_4^{Vi}$ and a rotary evaporator drying step at 150° C. in a vacuum of 5 mbar for 4 hours was added.

EXAMPLE 8.2

Production of Grafted Silica with a Mixture of Cyclotetrasiloxane and Vinyl Cyclotetrasiloxane (Ex 8.2)

The same method as for example 2 was used, except that the 383.01 g of $D_4$ was replaced by 378 g of $D_4$ and 5 g of $D_4^{Vi}$ and a rotary evaporator drying step at 150° C. in a vacuum of 5 mbar for 4 hours was added.

Table II below shows the results of the characterisation of each of the silicas obtained in examples 6.1, 6.2, 6.3, 7, 8.1 and 8.2:

TABLE II

| Silica | Ethoxylation | | Mass loss with TGA | | |
|---|---|---|---|---|---|
| | % D | % $D^{vi}$ | <200° C. | between 200 and 450° C. | >450° C. |
| Ex 6.1 | 5.8 | 1.3 | 0.6 | 0.8 | 1.7 |
| Ex 6.2 | 5.2 | 1.2 | 0.6 | 0.8 | 2.0 |
| Ex 6.3 | 3.9 | 3.0 | 0.6 | 0.6 | 1.6 |
| Ex 7 | 0.3 | 48.0 | 21.1 | 3.2 | 6.9 |
| Ex 8.1 | 11.7 | 0.2 | 0.2 | 1.7 | 3.5 |
| Ex 8.2 | 8.3 | 0.5 | 0.4 | 1.7 | 3.3 |

% D: mass percentage of D siloxy units having the formula $(CH_3)_2SiO_{2/2}$;
% $D^{vi}$: mass percentage of vinyl D siloxyl units having the formula $(CH_3)(vinyl)SiO_{2/2}$.

The results shown in table II demonstrate that it is possible, using the method according to the invention, to graft a functionalised organosilane compound on the surface of the silica. Ethoxylation demonstrates for each example that the graft consists of vinyl D groups ($D^{Vi}$ having the formula $(R^1)(vinyl)SiO_{2/2}$) on the surface.

Examples 6.1 to 6.3 and 8.1 and 8.2 according to the invention, demonstrate that it is possible to obtain a mixed graft with a non-functionalised organosilane compound and a functionalised organosilane compound, notably a vinyl compound on the silica surface, thus suitable for modulating the vinyl group content on the surface, making it possible to modulate the properties of the hot crosslinkable elastomers obtained using the silica according to the invention. This mixed graft exhibits the same characteristics as for the silicas Ex 2 to Ex 4, i.e. a large proportion of $D^{OH}$ groups and a small proportion of "mobile" D groups.

The TGA of the silica Ex 7 shows a mass loss between 200 and 450° C. greater than that generally obtained with silicas obtained using the method according to the invention, and the NMR spectrum shows a large proportion of "mobile" $D^{Vi}$ groups, indicating that under the conditions of example 7, the grafting obtained could comprise a portion of non-chemically grafted vinyl linear organosilane compound.

EXAMPLE 9

Hot Crosslinkable Silicone Elastomer Compositions (HCE) Based on Modified Silica According to Examples 2 to 5, 7, 8.1 to 8.2, and According to Comparative Examples 1 to 4

The various silicone elastomer compositions were formulated on the basis of the following formulation:
  67.4% by weight of vinyl polydimethylsiloxane (PDMS) gum (molecular mass as weight=500 kg/mol and molecular mass as number=200 kg/mol),
  1.4% by weight of a hydroxylated PDMS oil,
  30.6% of optionally modified silica,
  0.6% by weight of catalyst: an organic peroxide (2,5-dimethyl-2,(-di(tertiobutylperoxy)hexane) filled to 75% by mass in silica gel.

Each composition was prepared in a MEILI type mixer for 50 min. The peroxide was then added to the composition using a duplex mixer, and the composition was crosslinked under pressure for 10 min at 175° C.

After 24 hours, test specimens corresponding to each composition were punched out (non-annealed elastomer (NA)).

Annealing for 4 hours at 200° C. was also applied to each of the compositions and test specimens were cut out after 24 hours (annealed elastomer (A)).

On each test specimen, tensile tests were performed as per the standard ASTM D412. These tests make it possible to obtain the breaking properties (such as the stress and elongation), but also the measurement of the modulus at 100%. Further tests, such as the tear strength and the hardness measurement, were conducted. A visual assessment of the transparency was also performed. It consisted of positioning a silicone sheet 15 cm from a legible text and assessing whether the text is easy to read or not. The quality is enhanced according to the following scale: (−−), (−), (+) (++), where (−−) is the worst result and (++) is the best result. The results of theses tests and measurements (including the standard deviations annotated SD) are shown in table III below.

TABLE III

| | Hardness | Tear strength | | Stress at break | | Elongation at break | | Modulus at 100% | | Trans- |
|---|---|---|---|---|---|---|---|---|---|---|
| | ShA | N/mm | SD | MPa | SD | % | SD | MPa | SD | parency |
| Ex 2 (NA) | 45.3 | 20.3 | 1.0 | 8.0 | 0.1 | 655 | 7 | 0.8 | 0.0 | + |
| Ex 2 (A) | 55.9 | 21.4 | 1.3 | 10.5 | 1.4 | 554 | 48 | 1.2 | 0.0 | |
| Ex 3 (NA) | 56.4 | 16.9 | 0.1 | 6.3 | 0.8 | 477 | 37 | 1.5 | 0.1 | − |
| Ex 3 (A) | 62.0 | 16.3 | 0.5 | 5.3 | 0.5 | 284 | 21 | 2.4 | 0.1 | |
| Ex 4 (NA) | 52.4 | 17.4 | 0.3 | 8.9 | 0.4 | 661 | 21 | 1.0 | 0.0 | − |
| Ex 4 (A) | 62.6 | 18.3 | 0.6 | 8.5 | 1.0 | 419 | 22 | 1.8 | 0.0 | |
| Ex 5 (NA) | 52.0 | 12.8 | 0.1 | 4.7 | 0.3 | 490 | 19 | 1.1 | 0.0 | − |
| Ex 5 (A) | 56.6 | 14.6 | 0.2 | 5.3 | 0.4 | 420 | 23 | 1.5 | 0.0 | |
| C-Ex 1 (NA) | 42.4 | 19.8 | 0.5 | 6.9 | 0.4 | 619 | 21 | 0.7 | 0.0 | + |
| C-Ex 1 (A) | 53.9 | 22.2 | 1.4 | 10.7 | 0.8 | 598 | 36 | 1.1 | 0.0 | |
| C-Ex 2 (NA) | 46.4 | 18.1 | 2.4 | 5.4 | 0.3 | 541 | 19 | 0.9 | 0.0 | − |
| C-Ex 2 (A) | 53.2 | 18.4 | 0.2 | 5.8 | 0.2 | 453 | 13 | 1.2 | 0.0 | |
| C-Ex 3 (NA) | 71.6 | 22.9 | 0.6 | 9.2 | 1.2 | 513 | 35 | 1.5 | 0.0 | |
| C-Ex 3 (A) | 79 | 21.7 | 0.4 | 7.7 | 0.6 | 303 | 16 | 2.5 | 0.0 | |
| C-Ex 4 (NA) | 46.0 | 19.8 | 0.3 | 7.5 | 0.5 | 615 | 26 | 0.8 | 0.0 | |

TABLE III-continued

|  | Hardness | Tear strength | | Stress at break | | Elongation at break | | Modulus at 100% | | Trans- |
|---|---|---|---|---|---|---|---|---|---|---|
|  | ShA | N/mm | SD | MPa | SD | % | SD | MPa | SD | parency |
| C-Ex 4 (A) | 54.1 | 22.6 | 1.1 | 11.4 | 0.3 | 612 | 14 | 1.1 | 0.0 |  |
| Ex 7 (NA) | 82.9 | 20.6 | 0.8 | 3.7 | 0.1 | 67 | 7 | — | — | -- |
| Ex 7 (A) | 85.0 | 21.1 | 2.4 | 3.7 | 0.1 | 69 | 6 | — | — |  |
| Ex 8.1 (NA) | 49.1 | 21.3 | 0.9 | 9.5 | 0.4 | 572 | 12 | 1.1 | 0.0 | + |
| Ex 8.1 (A) | 54.3 | 21.8 | 1.5 | 9.3 | 0.7 | 472 | 21 | 1.4 | 0.0 |  |
| Ex 8.2 (NA) | 59.0 | 19.9 | 0.6 | 9.7 | 0.6 | 417 | 18 | 1.9 | 0.0 | ++ |
| Ex 8.2 (A) | 63.0 | 19.2 | 0.3 | 9.8 | 0.5 | 381 | 15 | 2.2 | 0.0 |  |

(NA): non-annealed elastomer after crosslinking for 10 min at 170° C.
(R): annealed elastomer (annealing for 4 hours at 200° C. after cross-linking for 10 min at 170° C.)
SD: Standard Deviation The results obtained with the silica from Ex 2 demonstrate that the treatment is effective, insofar as it reduces interactions between the silica and the silicone matrix. Indeed, the elastomer obtained with the unprocessed silica C-Ex 3 has a much higher Shore A hardness and modulus at 100% than for the elastomer reinforced with silica from Ex 2. The stress at break is relatively similar for both elastomers, but the treatment makes it possible to obtain a greater elongation at break. It is also important to note that the dispersion of the unprocessed silica C-Ex 3 is much longer than for the modified silica; approximately five times more time was required to incorporate all the unprocessed silica into the silicone gum. Furthermore, the silica/gum mixture is much harder and more difficult to shape with the silica C-Ex 3 than with the silica Ex 2. The treatment with $D_4$ according to the invention thus facilitates the incorporation of the silica and makes it possible to reduce silica/gum interactions.

Furthermore, the elastomer obtained with the silica Ex 2, exhibits quasi-identical properties to those of the elastomer reinforced with the silica C-Ex 4 which is modified by spraying $D_4$ and heat treatment (both in terms of mechanical properties and transparency of the elastomer). The method according to the present invention is thus suitable for performing filler treatments with equal performances to those performed industrially.

The properties of the elastomer reinforced with silica Ex 4 are satisfactory, but slightly different (to those of the elastomer reinforced with silica Ex 2 or C-Ex 4). The silica is less treated and is thus more reinforcing, conveyed by a higher modulus at 100% and hardness, a similar stress at break and a lower elongation at break.

The results obtained with the silica according to examples 3 and 5 (Ex 3 and Ex 5) are less satisfactory, since the silica is poorly dispersed. In the first case, this is explained by insufficient grafting, and the silica is still too hydrophilic to be finely divided after the drying step. In the second case, this is explained by excessive grafting which appears to have an adverse effect on the dispersion.

The elastomers reinforced with the silicas C-Ex 1 and C-Ex 2 have completely different properties. Indeed, it should be noted that the silica C-Ex 2 is dispersed very poorly, which reduces the mechanical properties thereof dramatically. This is explained by an excessively high grafting ratio on the surface of the silica C-Ex 2.

The silicas obtained using the method according to the invention may compete with industrial silicas such as the silica C-Ex 4. However, a further advantage of this invention (in addition to the fact that it is produced in a neutral medium) is that it is further possible to introduce vinyl groups in addition to the D groups on the surface.

Adding vinyl groups on the surface (Ex 8.1 and Ex 8.2) makes it possible to modulate the properties of silicones with a constant silica content. In this way, for the same silica concentration, an increase in the vinyl constant increases the hardness more particularly for non-annealed mixtures, along with s and the modulus at 100%. A further effect of the presence of these vinyl groups is that as the number of vinyl groups on the surface increases, the difference between the properties of the elastomer before and after annealing decreases. For example, with the silica Ex 8.2, the properties after crosslinking are very similar to those obtained after annealing. For these elastomers reinforced with mixed grafting silica, the stress at break remains similar, but the elongation at break decreases due to increased crosslinking of the elastomer network.

The transparency of the silicone elastomers is also enhanced, notably when the silica has mixed grafting of non-functionalised organosilane compound and vinyl organosilane compound (silica Ex 8.2). It would appear that the presence of vinyl groups chemically bound with the surface (as permitted by the invention) makes it possible to enhance the transparency.

The silica Ex 7 is dispersed very poorly due to the high grafting ratio thereof (as for the silicas Ex 5 and C-Ex 2). This explains the poor mechanical properties of the elastomer reinforced with the silica obtained in example 7.

The invention claimed is:

1. A method for preparing a silica grafted with at least one organosilicon compound chosen from the group consisting of:
   a cyclosiloxane, and
   a polyorganosiloxane having the following formula (I):

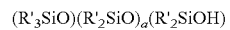
   $(R'_3SiO)(R'_2SiO)_a(R'_2SiOH)$ wherein:
      the groups R', identical or different, represent a $C_1$-$C_{10}$ alkyl group, an alkenyl group, an aryl group, or an —OH group,
      and the symbol a is an integer between 1 and 30,
   and mixtures thereof;
   said method comprising the following steps:
   a) the preparation of an aqueous mixture having a pH between 6 and 11, by adding in an aqueous medium a silica and optionally a base,
   b) the said organosilicon compound is added to the mixture,
   c) the mixture is refluxed for a time greater than or equal to 1 hour at a temperature between 50° C. and 100° C., and
   d) the grafted silica is separated from the mixture.

2. The method according to claim 1 comprising a further step a') performed between steps a) and b) consisting of adding to the mixture:

a water-miscible solvent compatible with said organosilicon compound so as to facilitate contact between the organosilicon compound and the silica, and/or a salt.

3. The method according to claim 2, wherein the % by weight of the salt/silica ratio is between 0.1 and 10%.

4. The method according to claim 2 wherein the water-miscible solvent is selected from the group consisting of ethanol, isopropanol, tetrahydrofuran, methyl ethyl ketone, and mixtures thereof.

5. The method according to claim 2 wherein the salt is selected from the group consisting of sodium, potassium, ammonium, pyridinium salts and mixtures thereof.

6. The method according to claim 1 comprising a further step c') performed between steps c) and d) consisting of adding a non-water miscible solvent to the mixture.

7. The method according to claim 1 wherein the following steps are performed after step d):

e) the grafted silica from step d) is dried, and f) the grafted silica is ground.

8. The method according to claim 1 wherein the silica is fumed silica.

9. The method according to claim 1 wherein the cyclosiloxane has the following formula (II):

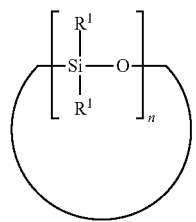

(II)

where:

n=3, 4, 5, 6, 7 or 8; and:

if the cyclosiloxane is a non-functionalised cyclosiloxane, the symbols $R^1$, identical or different, represent an optionally substituted linear or branched $C_1$-$C_{12}$ alkyl radical, an optionally substituted $C_5$-$C_{10}$ cycloalkyl radical, an optionally substituted $C_6$-$C_{18}$ cycloalkyl radical or an optionally substituted aralkyl radical, and if the cyclosiloxane is a functionalised cyclosiloxane, at least one of the symbols $R^1$ represents an alkenyl radical.

10. The method according to claim 9 wherein the cyclosiloxane is selected from the group consisting of octamethylcyclotetrasiloxane, and tetramethyltetravinylcyclotetrasiloxane and mixtures thereof.

11. The method according to claim 9 wherein the mixture of organosilicon compounds comprises:

at least one non-functionalised cyclosiloxane having formula (II) as defined according to claim 9, and at least one functionalised cyclosiloxane having formula (II) as defined according to claim 9.

12. A silica grafted with at least one organosilicon compound capable of being obtained by the method according to claim 1, wherein said grafted silica is characterized by the presence on the surface of Si—O-g functions where G is a siloxane graft comprising:

i) at least two siloxyl D units having the formula $(R^1)_2$ $SiO_{2/2}$, and ii) one terminal siloxyl $D^{OH}$ unit having the formula $(R^1)_2$ $(OH)SiO_{1/2}$, wherein the symbols $R^1$, identical or different, represent an optionally substituted linear or branched $C_1$-$C_{12}$ alkyl radical, an optionally substituted $C_5$-$C_{10}$ cycloalkyl radical, an optionally substituted $C_6$-$C_{18}$ aryl radical or an optionally substituted aralkyl radical or an alkenyl radical.

13. The grafted silica according to claim 12 wherein the siloxane graft G comprises between 2 and 31 siloxyl D units and at least one terminal siloxyl $D^{OH}$ unit.

14. The grafted silica according to claim 12 characterised by the presence on the surface of Si—O-G functions where G is a siloxane graft comprising:

i) 3 siloxyl D units having the formula $(CH_3)_2 SiO_{2/2}$ and 1 $D^{OH}$ terminal siloxyl unit having the formula $(CH_3)_2$ $(OH)SiO_{1/2}$, or ii) 3 siloxyl $D^{Vi}$ units having the formula $(CH_3)$ $(CH_2=CH_2-)SiO_{2/2}$ and 1 $D^{OH}$ terminal siloxyl unit having the formula $(CH_3)_2(OH)SiO_{1/2}$.

15. A silicone elastomer obtained by crosslinking a composition crosslinkable into an elastomer, said composition comprising at least grafted silica as defined according to claim 14.

16. An article comprising a silicone elastomer as defined according to claim 15.

17. The grafted silica according to claim 12 characterised by:

i) thermogravimetric analysis (TGA) with a temperature rise of 50° C. per minute and measured between 200° C. and 450° C., of a mass loss greater than or equal to 0.55%, ii) thermogravimetric analysis (TGA) with a temperature rise of 50° C. per minute and measured at a temperature greater than 450° C., of a mass loss obtained greater than 1.1%, and iii) the presence of a peak between −5 and −15 ppm in a spectrum obtained by means of nuclear magnetic resonance of the chemical element $^{29}Si$ in the solid state.

18. A silicone composition crosslinkable into an elastomer comprising at least one grafted silica as defined according to claim 12.

19. The composition according to claim 18 characterised in that the content by weight of grafted silica in relation to the total weight of the composition is between 0.1 and 80% by weight.

20. A toothpaste composition comprising a grafted silica as defined according to claim 12.

21. An anti-foaming composition comprising a grafted silica as defined according to claim 12.

22. The method according to claim 1 wherein in step c), the mixture is refluxed for a time greater than or equal to 20 hours.

* * * * *